United States Patent [19]

Bellotti et al.

[11] Patent Number: 4,738,668
[45] Date of Patent: Apr. 19, 1988

[54] CONDUIT CONNECTORS HAVING ANTISEPTIC APPLICATION MEANS

[75] Inventors: Marc Bellotti, Winnetka; Dean G. Laurin, Lake Zurich; Ronald C. Stauber, Hawthorn Woods; Larry C. Taylor, McHenry, all of Ill.

[73] Assignee: Baxter Travenol laboratories, Inc., Deerfield, Ill.

[21] Appl. No.: 527,604

[22] Filed: Aug. 29, 1983

Related U.S. Application Data

[62] Division of Ser. No. 288,224, Jul. 29, 1981, Pat. No. 4,432,766.

[51] Int. Cl.$^4$ .............................................. A61M 25/00
[52] U.S. Cl. ...................................... 604/283; 604/29; 604/905
[58] Field of Search ................... 604/23, 29, 265, 283, 604/905, 405, 305; 128/1 R; 422/28, 29, 34, 37, 40, 211, 300, 305

[56] References Cited

U.S. PATENT DOCUMENTS

| | | | |
|---|---|---|---|
| 3,848,603 | 11/1974 | Throner | 604/54 |
| 3,957,082 | 5/1976 | Fuson et al. | 604/80 |
| 4,209,013 | 6/1980 | Alexander et al. | 604/29 |
| 4,242,310 | 12/1980 | Greff et al. | 422/300 |
| 4,306,976 | 12/1981 | Bazzato | 604/29 |
| 4,340,049 | 7/1982 | Munsch | 604/29 |
| 4,353,367 | 10/1982 | Hunter et al. | 604/905 |
| 4,412,834 | 11/1983 | Kulin et al. | 604/283 |

OTHER PUBLICATIONS

G. Sykes, "Disinfection and Sterilization" 1958, D. Van Nostrand Co., Inc. (Great Britain), pp. 169-170, 200-201, 208, 308-333.

A. Torricelli, "Sterilization of Empty Containers for Food Industry", Ozone Chemistry and Tech., 1959, Amer. Chem. Soc. (Wash., D.C.), pp. 375-380.

A. Redniss, "HCl Oxidation Processes", Chlorine, Its Manufacture Properties and Uses, 1962, Reinholt Pub. Co. (NY), pp. 250-272.

*Primary Examiner*—C. Fred Rosenbaum
*Assistant Examiner*—H. Macey
*Attorney, Agent, or Firm*—Paul C. Flattery; Charles R. Mattenson; Garrettson Ellis

[57] ABSTRACT

A pair of separate conduits, each having an internal seal zone, may be joined by the method which comprises sealingly joining the ends of the conduits together; thereafter adding an antiseptic into the area of the joined conduits between internal seals formed in the zones; and then opening said internal seals without separating the conduits to permit internal fluid flow through the joined conduits.

8 Claims, 3 Drawing Sheets

CONDUIT CONNECTORS HAVING ANTISEPTIC APPLICATION MEANS

This is a division of application Ser. No. 288,224, filed July 29, 1981, now U.S. Pat. No. 4,432,766.

TECHNICAL FIELD

The medical procedure known as continuous ambulatory peritoneal dialysis (CAPD), described in U.S. Pat. No. 4,239,041, has rapidly grown in clinical acceptance as the technique of choice for maintaining many patients who have lost kidney function. Peritoneal dialysis solution is inserted in the peritoneal cavity, whereby diffusion exchange takes place between the solution and the bloodstream across the peritoneal membrane, to remove by diffusion the waste products which are normally excreted through the kidneys, typically solutes such as sodium and chlorine ions and the other materials normally excreted by the body such as urea, creatinine and water.

In the CAPD technique, the patient is surgically equipped with an implanted catheter which communicates between the peritoneal cavity and the exterior. Peritoneal dialysis solution is passed into the peritoneal cavity where dialysis of urea and the like takes place between the solution and the blood passing through blood vessels in the peritoneum, which is the lining of the peritoneal cavity. Thereafter, this peritoneal dialysis solution is removed from the peritoneal cavity, carrying with it diffused breakdown products from the blood. Fresh dialysis solution is then passed into the peritoneal cavity, and this process of filling and emptying is repeated several times.

In the CAPD technique, as with all techniques of peritoneal dialysis, peritonitis is one of the most significant risks. Peritonitis can result if connections are made between the peritoneal catheter and a set communicating with a source of dialysis solution in a manner which permits even a very small number of microorganisms to enter the catheter and to be flushed in the peritoneal cavity.

Accordingly, the frequent connections which must be made and broken between the catheter residing in the peritoneal cavity and a succession of dialysis solution containers must be performed in a manner which permits sterile connections to be made. In this procedure, as well as many other procedures in the medical field and the like, such sterile connections are highly desirable, for example for tubular connections between conduits for flow of liquids, gases and solids.

As examples of such other areas where sterile connections are desirably made, and in which the invention of this application may be used, one can include the processing of blood and its fractions, the mixing of sterile solutions, connecting Foley catheters with urinary drainage bags, and hemodialysis or blood oxygenation procedures especially with patients who have diminished immunological capability. Also, the invention may be used to provide sterile conditions to a protective enclosure surrounding an indwelling catheter or the like.

The word "sterile" as used herein is intended to include not only its accustomed meaning of a total absence of living microorganisms, but also is intended to include the concept of substantial sterility, in which the number of microorganisms is reduced to such a low population that the likelihood of infection or contamination, i.e., peritonitis in the case of CAPD, is substantially reduced or eliminated.

BACKGROUND ART

The use of antiseptic for sterilization while making connections in CAPD and similar procedures is broadly used with the Beta-Cap of the Quinton Instrument Company, which is a closure for the end of a CAPD catheter. The tubing adjacent the closure is clamped from the outside. The tube end is filled with a liquid antiseptic, for example the well known providone iodine, and the cap is placed on the end of the catheter. To open the catheter, the cap is removed; the antiseptic is drained out; and the connection is made.

Throner U.S. Pat. No. 3,848,603 teaches medical apparatus in which antiseptic is metered to a flow line to provide an antiseptic barrier to suppress microorganism growth in the material, which is typically a body waste being drained from the body.

Also there is a process in wide-spread commercial use to sterilize the inside of packages containing surgical dressings and a wide variety of medical products, using ethylene oxide gas. The ethylene oxide gas diffuses through a porous section of the package containing the product. This porous section prevents the passage of bacteria into the package, but allows passage of ethylene oxide gas into the package, to sterilize the package contents.

Schlesinger U.S. Pat. No. 3,605,752 discloses a catheter guard for fitting around a catheter having a sponge portion which may be impregnated with an antibacterial agent so that retrograde contamination of bacteria about the outside surface of the catheter into the patient is prevented.

Mount U.S. Pat. No. 3,396,727 discloses a drainage tube for body fluids provided with filtering means coated with a antibacterial material.

Alexander et al. U.S. Pat. No. 4,209,013 discloses a flexible chamber into which the two conduits for connection are inserted, and antiseptic fluid is added to bathe the two conduit ends prior to bringing the two conduit ends together into connecting relation.

Greff et al. U.S. Pat. No. 4,242,310 discloses sterile connection apparatus in which a sealed box is provided with a rubber glove member attached so that connectors on the ends of a pair of conduits may be manually sterilized within the box prior to connection.

In the article by Yee et al. entitled "Use of Povidone Iodine in Continuous Ambulatory Peritoneal Dialysis (CAPD) A Technique to Reduce the Incidence of Infectious Peritonitis" Volume 26 *Trans Am. Soc. Artif. Inter. Organs* pp. 223–224, 1980, the use of povidone iodine as a sterilizing agent in making connections with the dialysis solution bag in CAPD is taught. A small, flexible bulb just below the spike is provided to permit aspiration of povidone iodine into the line during dialysis solution bag exchanges.

By this invention, significant improvements are provided in the joining of conduits together by means of connectors, where the closest possible approach to absolute sterility is obtained, but at the same time the patient can be protected from any toxic effect of the antiseptic.

DISCLOSURE OF THE INVENTION

In accordance with this invention, a method is provided for joining a pair of separate conduits, each having an internal closure in a seal zone which is spaced from the end to be joined. The method comprises sealingly joining the ends of the conduits together to define a sealed zone between the internal closures; thereafter adding an antiseptic into the sealed zone area of the joined conduits between the internal closures; and then opening the internal closures without separating the conduits, to permit internal fluid flow through the joined conduits.

Preferably an antiseptic which can be harmlessly inactivated by the material which flows through the conduits is used. For example, chlorine gas is generally inactivated by the sugar present in peritoneal dialysis solution in the case of CAPD, so that after the antiseptic application on the joined ends, the flow of such solution through the joined conduits quickly inactivates the residue of chlorine gas, so that no ill effects are experienced by the patient due to the sterilization step.

Preferably, the antiseptic is added as a gas to the area of the joined conduits between the internal closures through a port in at least one of the conduits, with the port being occluded by bacteria-blocking filter means, which may be a commercially available filter material, preferably hydrophobic in nature, having a pore size small enough to exclude bacteria but to permit the flow of the antiseptic gas therethrough.

As previously stated, in peritoneal dialysis and particularly CAPD processes, repeated connections and disconnections must be made between the set communicating with the peritoneal catheter and various solution containers. After connection, the solution is infused into the peritoneal cavity, and after the dwell period it is withdrawn again.

After the spent dialysis solution has been drained from the peritoneal cavity, the set and its connector may remain filled with liquid, retained by capillary attraction within the small bore of the tubing and connector. In this instance, one may internally close the first tubing or conduit, which communicates with the peritoneal cavity, draining any liquid remaining between this internal closure and the outer end of the conduit by venting air into the area through a port. This port is occluded by a bacteria-blocking filter of the type described above.

Thereafter, one may disconnect the bag of spent dialysis solution, and reconnect a bag of fresh dialysis solution which carries another tube or conduit which also defines an internal closure formed in its internal seal zone. Thus the first conduit connected to the peritoneal catheter forms a connected pair with a new conduit, each having internal closures as described above, to form a sealed zone between the internal closures. One may then add an antiseptic into the internal area of the sealed zone of the joined conduits, between the internal closures, for resterilization of the connection area, prior to flowing fresh dialysis solution through the connection area or sealed zone.

The fact that air is passed into the area as described above facilitates complete drainage of the sealed zone so that the sterilizing action of the antiseptic is not interfered with by the presence of a residue of dialysis solution.

The connector of this invention carried on the first conduit may have its usual bore or lumen for connection with the bore or lumen of another connector, plus first aperture means to serve as the antiseptic entry port for the abovedescribed process. This port will communicate between the exterior and the interior of the connector, and have the desired bacteria-blocking filter positioned therein. The first conduit connector also may have internal closure means for releasably sealing its interior without disrupting the sealing connection of it with another connector with which it mates. Thus a sterile connection area or sealed zone may be provided.

The chlorine gas or other desired preferably gaseous sterilizing material may be added from an ampule, particularly an ampule in which pressure is generated to force the gas into the system when desired. Alternatively, a syringe, squeeze bulb, or the like may be used. Alternative antiseptic gases may include bromine, iodine, chlorine oxides, a nascent oxygen such as ozone or atomic oxygen, or HClO vapor.

The antiseptic is adapted to flow through the connector's first aperture described above. The ampule from which the antiseptic is provided may be separable from this first aperture.

Typically, the ampule may include a strong acid and a rupturable cartridge containing an alkali carbonate salt and an alkali hypochlorite salt, to generate chlorine and carbon dioxide for pressurization upon breaking of the cartridge, with the result that the chlorine gas is forced into the interior of the connector for improved antibacterial effect. Alternatively the strong acid may be placed in the cartridge and the salts outside thereof, for equal results.

The types of strong acid which may be used in the ampule may include water solutions of preferably hydrochloric acid, or any other nontoxic acid which may yield physiologically acceptable reaction products after use, for example acetic or phosphoric acids.

The carbonate salt may include any of numerous carbonates or bicarbonates, physiologically tolerable under conditions for use, for example sodium, calcium, magnesium, or potassium carbonate, bicarbonate, or mixtures thereof. Similarly, the hypochlorite salt may typically include any suitable nontoxic alkali cation, including sodium, magnesium, calcium or potassium hypochlorite.

The ampule may be of otherwise generally conventional design, for example as shown in U.S. Pat. No. 4,013,422. Upon rupturing of the cartridge wall, the acid mixes with the salt and generates chlorine, and carbon dioxide for pressurization, which gases pass out of the ampule and into the interior of the connector. After time is given for the chlorine to have its effect, for example a minute, the ampule may be removed, and the interior seals of the two conduits are opened to permit liquid flow. In the event the liquid is peritoneal dialysis solution, its sugar quickly consumes residual chlorine in the system. The liquid cannot pass out of the first aperture or antiseptic entry port because of the presence of the bacteria-blocking filter, which may be made of a commercially available hydrophobic filter so that aqueous liquids are also blocked from passage through the filter.

It is also desired that the first aperture (antiseptic entry port) of the connector be coverable at its outer end with a hinged cap, openable and closeable over it. Included with this may be jaw means, carried by the connector, for pinching shut the first conduit at a position adjacent the connector to define one of the internal seals or closures. Closure means may be carried on the connector to move between a first, closed position to seal the first conduit, and a second open position to allow flow through the conduit or tubing. These closure means can be jaws which seal the conduit when closed and leave it open when open. The closure means are positioned to be incapable of moving into the open position unless the hinged cap is in its closed position, to prevent the application of antiseptic through the antiseptic entry port while the closure means are open. This prevents accidental direct administration to the patient through the first conduit while the antiseptic is being injected into the sealed zone.

The first aperture means (antiseptic entry port) may also communicate with first longitudinal channel means defined within the connector, and extending from the first aperture means toward the forward end of the connector, the end which joins with the other connector. The first longitudinal channel means communicates at its forward end with the connector interior, and thus provides means for conveying the antiseptic to the forward end of the connector for desired sterilization effect.

It may be also desired for a second aperture means or vent to communicate between the exterior and interior of the connector, with the second aperture vent means communicating with the connector interior adjacent its rearward end, but forward of the closure means described above. This can be accomplished when the second aperture means is located at a longitudinal position on the connector between its ends and communicates with a second longitudinal channel defined within the connector. This channel extends from the second aperture means toward the rearward end of the connector. This structure may be used to provide venting of air out of the interior of the connector as well as for drainage of liquid from it in the manner described above. Also it facilitates the distribution of antiseptic gas administered under pressure by venting in the opposite direction as the gas is administered.

DESCRIPTION OF SPECIFIC EMBODIMENTS

Figure 1:
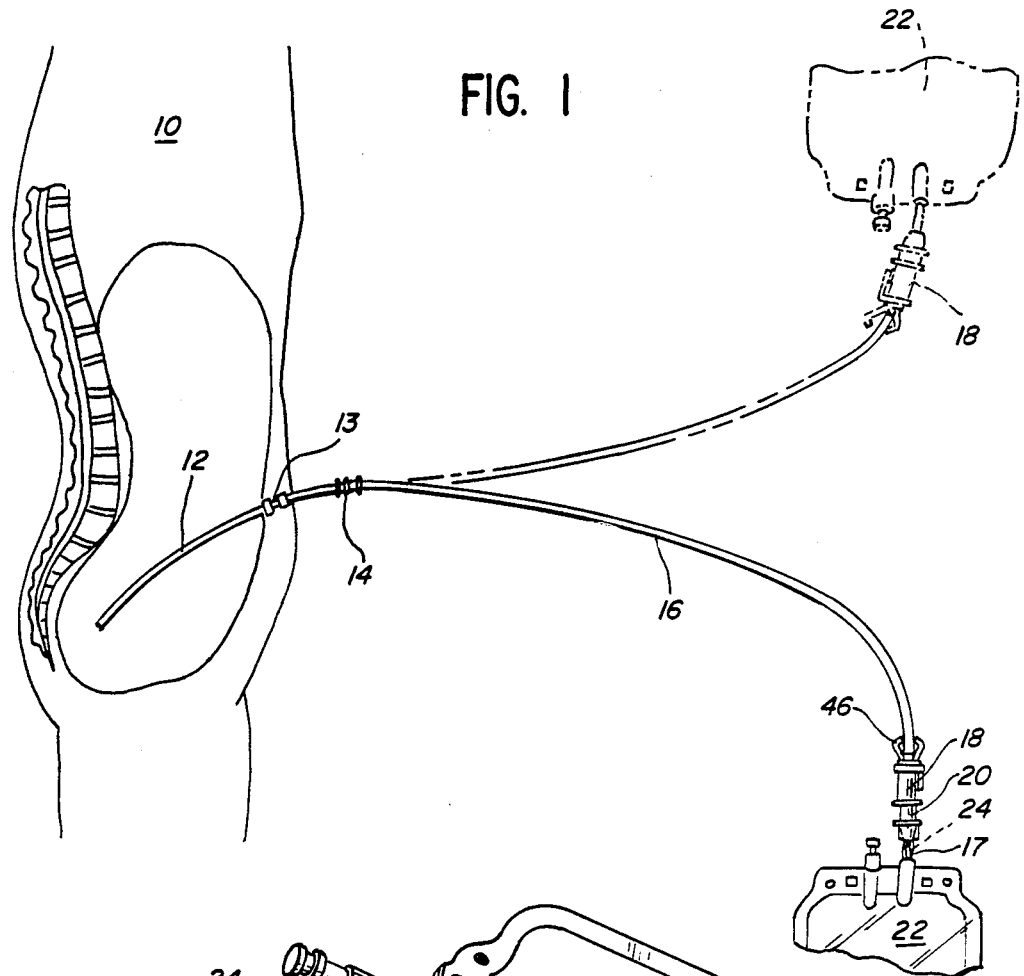
FIG. 1 is a schematic view showing the CAPD process in the infuse and drain stages of operation.
Figure 2:
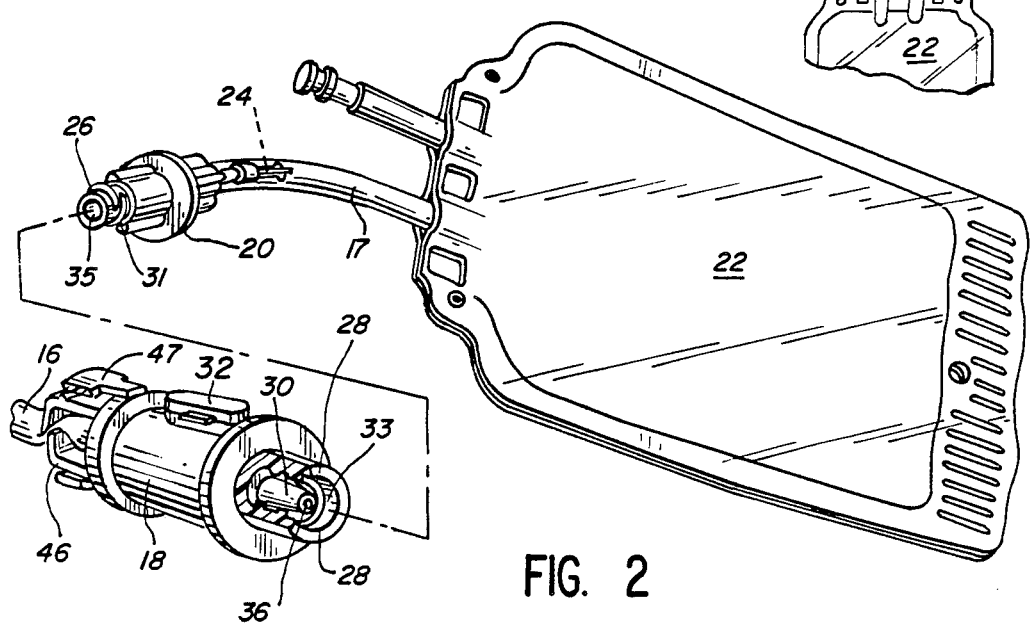
FIG. 2 is a perspective view of a peritoneal dialysis solution container utilizable in the CAPD process of FIG. 1 and showing in particular detail the container connector, and a mating connector that would be on the end of the tubing set attached to the catheter surgically implanted in the patient.
Figure 3:
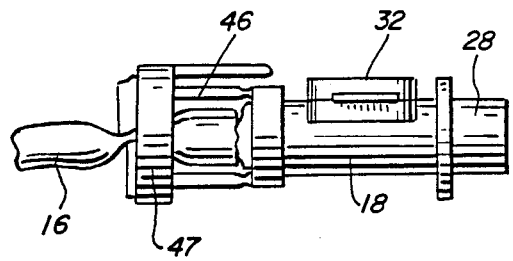
FIG. 3 is a detailed elevational view of the mating connector shown in FIG. 2, which is carried on the end of the set communicating with the implanted catheter.
Figure 4:
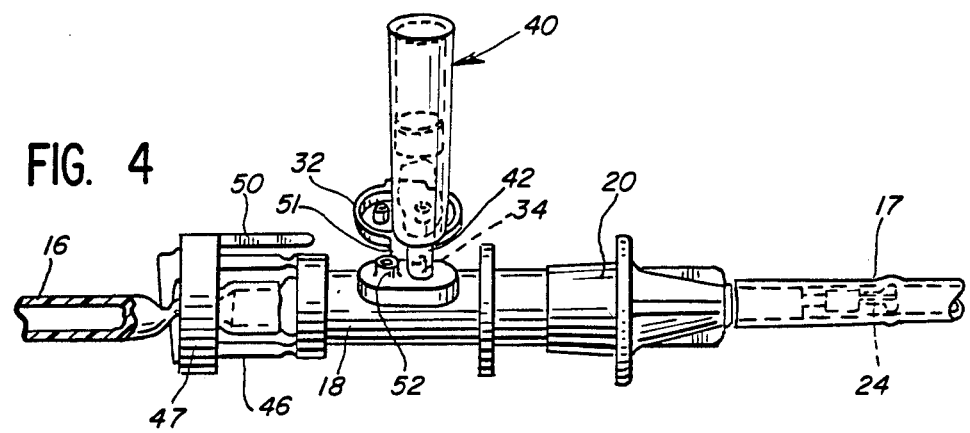
FIG. 4 is a fragmentary elevational view showing the two connectors of FIG. 2 in their connected relation with an ampule of chlorine gas that may be utilized in this invention, and showing the closure means as a sliding member with jaws, the jaws being in closed position.

Referring to FIGS. 1 through 6, FIG. 1 shows two phases of a typical peritoneal dialysis procedure, and particularly CAPD. The patient 10 carries a surgically implanted catheter 12 in his peritoneal cavity, the catheter being permanently secured in the skin by tissue ingrowth cuffs 13.

A tubular peritoneal dialysis extension set 16 is provided, secured to catheter 12 by connector 14 in a conventional manner, and typically replaced on a monthly basis by trained personnel in sterile manner. At the end of set 16 opposite connector 14 is a first connector 18 adapted for sealing, mating relation with a second connector 20. Connector 20 is carried in aseptic communication with peritoneal dialysis solution container or bag 22 on tubing 17. As shown, connector 20 may carry at its rear a frangible seal 24 which may be of a design as shown in U.S. Pat. No. 4,181,140, or it may be of the design as described in pending Munsch et al. U.S. application Ser. No. 086,102, filed Oct. 18, 1979.

The connectors 18, 20 fit together in mating, sealed relation with the forward portion 26 of connector 20 fitting into receptacle 28 of connector 18. Forward portion 26 of connector 20 defines screw threads 31 as shown for reliable sealing within member 28 of connector 18. Connector 18 defines internal mating threads 33. Projecting tube 30 of connector 18 fits within the bore 35 of member 26, so that the connectors 18 and 20 may fit together in sealing manner; for example as in Dennehey et al. Application Ser. No. 187,008, filed Sept. 14, 1980.

One of the connectors, particularly connector 18, may carry a hinged cap 32 which is openable and closeable over first aperture means 34. First aperture means 34 communicates between the exterior and the interior of bore 36 of connector 18. First aperture 34 carries a bacteria-blocking filter 38 across its orifice to permit the migration of gases into and out of the aperture but to prevent the passage of bacteria. Filter means 38 may be a conventional hydrophobic 0.22 micron filter material of a type commercially used in biomedical devices, with its hydrophobic properties preventing the migration of aqueous liquids through the filter. Therefore, liquids will not leak out of the first aperture 34 even if hinged cap 32 is open.

Figure 5:
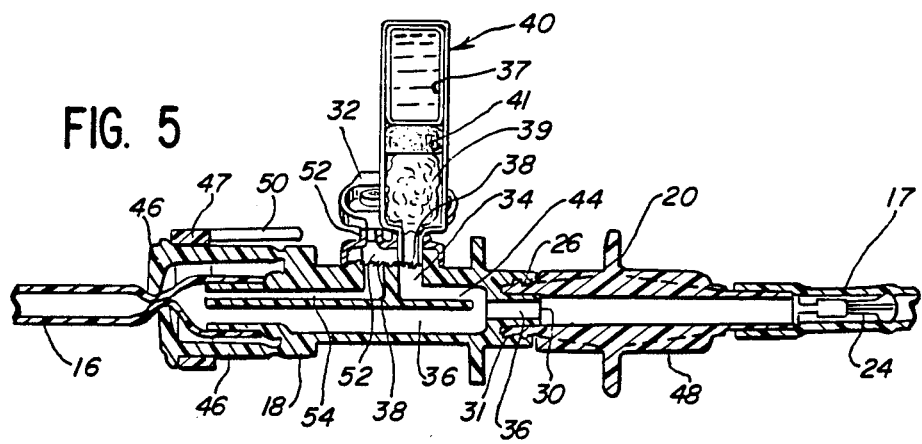
FIG. 5 is a view similar to FIG. 4, but taken partly in longitudinal section to show the interior of the structure.

Ampule 40 is provided, being structurally of conventional design and proportioned at its front end 42 for communication with first aperture 34. Ampule 40 preferably contains a strong acid such as a 1.5N aqueous hydrochloric acid solution positioned inside of a rupturable glass cartridge, for example, with a mixture of calcium hypochlorite and sodium bicarbonate placed in the ampule but outside of the rupturable cartridge. As in the design of conventional ampules (for example, Marion Scientific Type "C" $CO_2$ generator), the glass cartridge 37 holding the acid can be broken from the exterior by manual manipulation of the flexible, outer housing to cause the acid to mix with the solid salts 41. The result of this is to generate both chlorine and carbon dioxide which forces the chlorine gas through cotton wad 39 of the ampule, hydrophobic filter 38, and first aperture 34, and therefore inside of connector 18 with longitudinal conduit 44. Conduit 44 joins with bore 36 near the forward end of connector 18. During this step of the application of chlorine, breakaway member 24 is preferably not yet broken away, to seal that end of the chamber. Plastic jaws of closure means 46, which may be integrally molded with plastic connector 18, are held in a closed position as shown in FIG. 5 by sliding collet 47 to seal the flexible tubing of set 16, so that the area defined by bores 36 and 48 of connectors 18 and 20 is sealed or isolated from the rest of the flow path between the patient and the solution bag 22. The chlorine gas is delivered to a central location of this isolated area or sealed zone, and diffuses quickly throughout the area to exert its antibacterial effect throughout.

As gas is generated, the ampule and connectors may be rotated into an inverted position from that shown in the drawings so gas can easily pass upward from the ampule and into sealed zone area.

Figure 6:
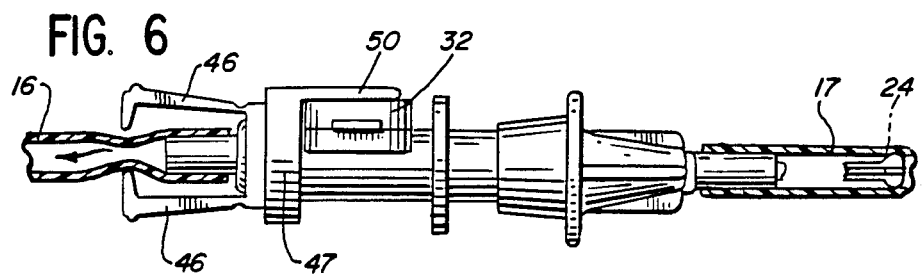
FIG. 6 is a view similar to FIG. 4, but showing the closure means in a position permitting opening of the jaws to allow fluid flow through the device.

When the chlorine gas has completed the sterilization process of the sealed zone area, ampule 40 may be removed, and hinged cap 32 may sealingly close over apertures 42 and 52. Collet 47 may then be retracted from its jaw-closing position. Extending plate member 50 of collet 47 is positioned to strike cap 32 or its hinge 51 in the event that hinged cap 32 is open at the time it is desired to draw collet 47 back from its jaw-closing position. However, when cap member 32 is closed, extending plate member 50 can pass over it as shown in FIG. 6 to permit opening of jaws 46 and the corresponding flow of liquid. Thus it becomes essentially impossible to accidentally leave jaws 46 in their open position while chlorine is being infused into the system.

One can then snap off breakaway member 24 to open the conduit 17, to provide an open flow path between the newly attached peritoneal dialysis solution bag 22 and the peritoneal cavity of the patient. Fresh dialysis solution can then flow into the peritoneal cavity of the patient, the dissolved sugar of which quickly reacts with any residual chlorine present, so that the resulting mixture received by the patient is essentially nontoxic.

As shown in FIG. 1, a typical peritoneal dialysis technique involves placing bag 22 in an initial, upper position to infuse fresh peritoneal dialysis solution into the peritoneal cavity of the patient. After infusion a dwell phase of generally three or four hours takes place. During dwell diffusion exchange takes place between the membrane of the peritoneal cavity and the dialysis solution in the peritoneal cavity. In the CAPD process, bag 22 is often not disconnected between infusion and dwell, but instead the patient wears it folded against his body under his clothes during dwell. This reduces the connections and disconnections which must be made.

After dwell, the bag 22 is placed at its lower position as shown in FIG. 1, and the spent peritoneal dialysis solution is allowed to drain from the patient's peritoneal cavity.

After this drain phase, connectors 18 and 20 may be disconnected, and a fresh bag of peritoneal dialysis solution 22 with its connector 20 may be attached.

Preferably prior to disconnection and attachment of a new dialysis solution container 22, any residual liquid in bore 36 is drained by moving sliding collet 47 into a position to close jaws 46 and to seal tubing 16. Due to the presence of second aperture 52 (also occluded by hydrophobic, bacteria-blocking filter member 38 and optionally the same piece of filter member as occludes first aperture 34), complete venting of bore 36 can take place and thus draining of it is easily accomplished, even when jaws 46 are closed. This provides reliable removal of liquid from bore 36 of connector 18.

Second aperture 52 communicates with an inner, longitudinal channel 54, which communicates with a rearward portion of connector 18 adjacent the clamping jaws 46. Optionally, chlorine gas may be inserted to the system through the second aperture 52 as well, or, in the alternative, second aperture 52 may be shaped so that ampule 40 cannot sealingly communicate therewith, to insure that the chlorine will not be accidentally injected through this aperture. For example, second aperture 52 may be made too large for a sealing fit.

After connection of a fresh dialysis solution bag 22 by the joining of connectors 18 and 20, the drained bore 36, and newly joined bore 48 are ready for an application of chlorine by means of another ampule of pressurized chlorine gas 40. After the application of the chlorine and a suitable period of time for the chlorine to sterilize the sealed zone, the breakaway connector 24 of the fresh bag 22 can be opened, ampule 40 can be removed, and collet 47 moved to a position allowing jaws 46 to open. Fresh dialysis solution can then pass into the patient's peritoneal cavity through the sterilized connection junction (previously the sealed zone) made in accordance with this invention in a reliable manner which reduces or eliminates the possibility of peritonitis.

Figure 7:
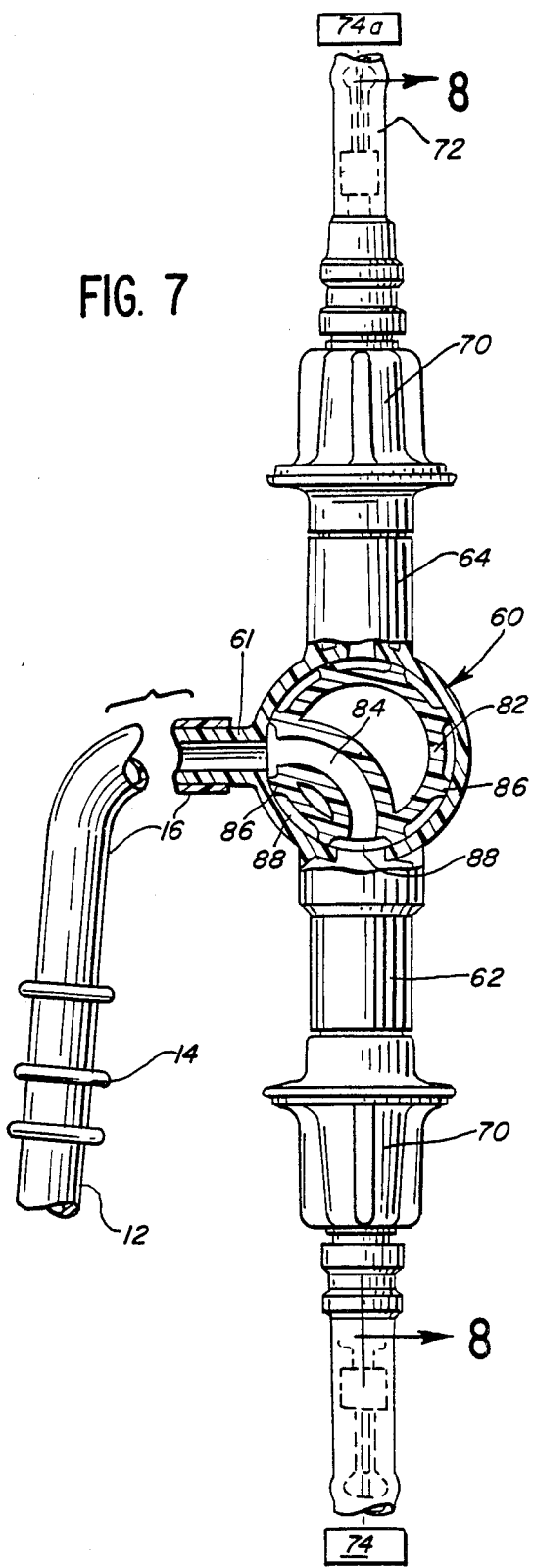
FIG. 7 is a plan view taken partly schematically of another embodiment of a connector system in accordance with this invention.
Figure 8:
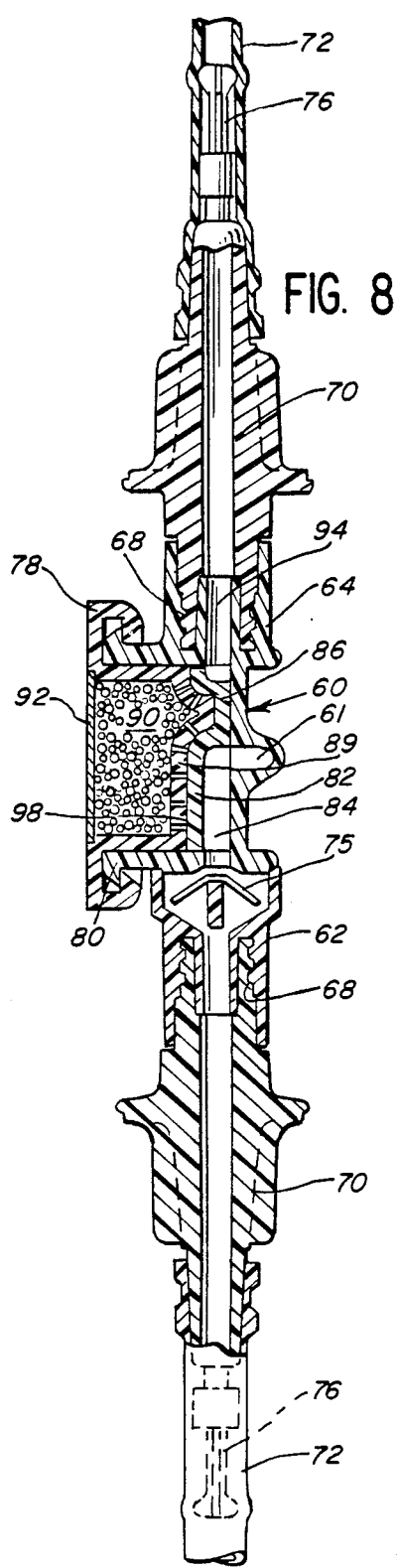
FIG. 8 is a longitudinal sectional view of the connector system taken along line 8—8 of FIG. 7.

Referring to FIGS. 7 and 8, another embodiment of the invention is disclosed. The tubing 16 at the end of peritoneal catheter 12 is shown communicating with port 61 of multiple-way valve means 60. This valve means may communicate optionally with a plurality of conduits 62, 64, for selectively permitting and preventing flow between the respective conduits. Each of conduits 62, 64 defined by the multiple-way valve 60 carries threads 68 on its inner surface so that it can be threadedly connected with matching external threads on connectors 70. Each connector 70 communicates with tubing 72 which in turn may communicate with a container 74, 74a for peritoneal dialysis solution or the like. One way drain valve 75 may also be provided.

In the infusion phase of CAPD, an internal breakaway member 76 is present in each connector 70. This member 76 is of a design similar to that previously disclosed as frangible seal 24. Accordingly, flexing of flexible tubing 72 will break away the frangible seal 76 and open the connection.

Multiple-way valve 60 carries a cover member 78 which interlocks in rotational relation with a base member 80 as shown, so that the valve interior may be turned.

Silicone rubber seal member 82 is defined having a bottom which in turn defines channel member 84 which is proportioned to sequentially interconnect port 61 with the respective apertures 62 and 64 for selective flow communication therebetween. Rotatable seal member 82 defines sealing protrusions 86 for providing a hermetic seal to channel 84, and between spaces 88 about the periphery of seal member 82. Seal 82 may be carried on perforated wall 89.

The space immediately above seal member 82, as shown in FIG. 8, within rotatable member 78 may be filled with a chlorine-releasing material 90 or other antiseptic. A filter member 92 may be positioned above the chlorine-releasing material to retain it. For example, the well known materials calcium hypochlorite, trichloro-s-triazinetrione (TCT), or chlorinated urea may be used as the chlorine-releasing material 90. In the case of TCT, when water is added, chlorine is generated, diffusing through the silicone rubber seal member 82 into the sealed zone 94 between the sealed pocket 88 and frangible seal 76, including the bore area within opening 64 and connector 70. The chlorine diffuses into the zone 94, sterilizing it and therefore the connection between conduit 64 and connector 70. Acids may also be used to generate chlorine.

As shown in FIG. 7, flow communication can remain intact between tubing 16 and conduit 62 of connector 70 while sterilization of zone 94 is taking place. This permits the drainage phase to take place simultaneously with the sterilization of zone 94 in preparation for the infusion phase.

With the embodiment of FIGS. 7 and 8, an antibacterial connection in accordance with this invention can be made by first rotating member 78 of the valve to close conduit 64, for example, of the valve means. A connection of conduit 64 with connector 70 may then be made, for example with a fresh bag of peritoneal dialysis solution. The system then only has to wait until the chlorine diffuses through bottom seal 82 into the zone 94 between the sealed member 82 and frangible seal 76, while the other conduits 61, 62 communicating with the valve 60 can continue to be utilized. Following this, after the antibacterial effect has been completed, frangible seal 76 may be opened, and the multiple-way valve means rotated so that conduit 64 enters into flow communication with conduit 61, so that peritoneal catheter 12 is in flow communication with container 74a. Then conduit 62 may be reconnected with another connector 70 and processed in similar manner.

It may be desired to selectively place foil strips 98 within or on the silicone rubber seal 82 of the rotatable valve portion 78, to restrict the diffusion of chlorine into undesired areas. For example, it may be undesired to allow chlorine to pass into channel 84, so a strip of polypropylene foil 98 can be added at this point along the surface of seal member 82. Also, flow ports may be placed in bottom seal 82 to accelerate antiseptic gas diffusion therethrough.

The above has been offered for illustrative purposes only, and is not intended to limit the scope of the invention, which is as defined in the claims below.

That which is claimed is:

1. In a connector carried on the end of a first conduit for sealingly connecting with another connector carried on another conduit, the improvement comprising:
 a portion of the first conduit within said connector being defined by a semipermeable wall member, a source of antiseptic which can penetrate through said wall member into the first conduit, means for retaining said source of antiseptic in a region communicating with the side of said wall member opposed to the first conduit, and means for blocking flow through said first conduit to permit the establishment of a sealed zone, including a portion of the first conduit into which the antiseptic can diffuse for antibacterial effect.

2. The connector of claim 1 in which multiple-way valve means are provided to selectively provide communication between said first conduit and a plurality of other conduits, said multiple-way valve means being capable of temporarily sealing any of said conduits.

3. The connector of claim 2 in which said semipermeable wall member is carried within said multiple-way valve means for selective rotation for providing communication between their respective conduits as desired.

4. The connector of claim 3 in which said semipermeable membrane wall carries impermeable strip members on a portion of its surface to selectively control the diffusion of antiseptic therethrough.

5. In a connector carried on the end of a first conduit, said connector having a solid, inner surface defining an inner space capable of providing communication between said first conduit and another conduit in communication with said connector, the improvement comprising, in combination: means associated with said connector for providing a diffusion of antiseptic through said solid, inner surface into said inner space for antibacterial effect.

6. The connector of claim 5 in which said antiseptic is chlorine gas.

7. The connector of claim 5 which carries a source of chlorine releasing material in a position adjacent said inner space, the chlorine released from said chlorine releasing material being capable of diffusion into said inner space.

8. The connector of claim 7 in which said chlorine releasing material is trichloro-s-triazinetrione.

* * * * *